(12) United States Patent
Backus et al.

(10) Patent No.: US 10,709,553 B2
(45) Date of Patent: Jul. 14, 2020

(54) V-CLIP POST WITH PIVOTING

(71) Applicant: BOSTON SCIENTIFIC SCIMED INC., Maple Grove, MN (US)

(72) Inventors: Andrew J. H. Backus, San Francisco, CA (US); Ali Salahieh, Saratoga, CA (US); Ning Pan, San Jose, CA (US); Stanley A. Carroll, San Carlos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 762 days.

(21) Appl. No.: 15/219,606

(22) Filed: Jul. 26, 2016

(65) Prior Publication Data
US 2017/0042671 A1 Feb. 16, 2017

Related U.S. Application Data

(60) Provisional application No. 62/204,067, filed on Aug. 12, 2015.

(51) Int. Cl.
*A61F 2/24* (2006.01)

(52) U.S. Cl.
CPC .......... *A61F 2/2418* (2013.01); *A61F 2/2409* (2013.01); *A61F 2/2427* (2013.01); *A61F 2/2436* (2013.01); *A61F 2/2439* (2013.01)

(58) Field of Classification Search
CPC .... A61F 2/2427; A61F 2/2412; A61F 2/2418; A61F 2/243; A61B 2017/00327; A61B 2017/00318
See application file for complete search history.

(56) References Cited

U.S. PATENT DOCUMENTS

| | | |
|---|---|---|
| 7,329,279 B2 | 2/2008 | Haug et al. |
| 7,381,219 B2 | 6/2008 | Salahieh et al. |
| 7,445,631 B2 | 11/2008 | Salahieh et al. |

(Continued)

FOREIGN PATENT DOCUMENTS

| | | |
|---|---|---|
| WO | 2005062980 A2 | 7/2005 |
| WO | 2005065585 A1 | 7/2005 |

(Continued)

OTHER PUBLICATIONS

International Search Report and Written Opinion, PCT/US2016/045505, dated Nov. 7, 2016.

*Primary Examiner* — Brian E Pellegrino
(74) *Attorney, Agent, or Firm* — Seager, Tufte & Wickhem LLP

(57) ABSTRACT

A replacement heart valve may include a tubular anchor member actuatable between an elongated delivery configuration and an expanded deployed configuration, a buckle member fixedly attached to the anchor member, a post member axially translatable relative to the buckle member, the post member including a latch portion configured to engage the buckle member when the anchor member is in the deployed configuration, an actuator member including a pivot pin proximate a distal end thereof, the actuator member being releasably connected to a proximal end of the post member at the pivot pin, and a valve leaflet attached to the post member. The post member may be disposed distal of the anchor member when the anchor member is in the elongated delivery configuration.

20 Claims, 11 Drawing Sheets

(56) References Cited

U.S. PATENT DOCUMENTS

| | | |
|---|---|---|
| 7,712,606 B2 | 5/2010 | Salahieh et al. |
| 7,748,389 B2 | 7/2010 | Salahieh et al. |
| 7,780,725 B2 | 8/2010 | Haug et al. |
| 7,824,442 B2 | 11/2010 | Salahieh et al. |
| 7,824,443 B2 | 11/2010 | Salahieh et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,182,528 B2 | 5/2012 | Salahieh et al. |
| 8,231,670 B2 | 7/2012 | Salahieh et al. |
| 8,246,678 B2 | 8/2012 | Salahieh et al. |
| 8,252,052 B2 | 8/2012 | Salahieh et al. |
| 8,287,584 B2 | 10/2012 | Salahieh et al. |
| 8,328,868 B2 | 12/2012 | Paul et al. |
| 8,343,213 B2 | 1/2013 | Salahieh et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,951,299 B2 | 2/2015 | Paul et al. |
| 8,992,608 B2 | 3/2015 | Haug et al. |
| 9,005,273 B2 | 4/2015 | Salahieh et al. |
| 9,011,521 B2 | 4/2015 | Haug et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2007/0162107 A1 | 7/2007 | Haug et al. |
| 2008/0125859 A1 | 5/2008 | Salahieh et al. |
| 2008/0234814 A1 | 9/2008 | Salahieh et al. |
| 2011/0257735 A1 | 10/2011 | Salahieh et al. |
| 2011/0276129 A1 | 11/2011 | Salahieh et al. |
| 2011/0282440 A1* | 11/2011 | Cao ............... A61F 2/2412 623/2.18 |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0330409 A1 | 12/2012 | Haug et al. |
| 2013/0013057 A1 | 1/2013 | Salahieh et al. |
| 2013/0123796 A1 | 5/2013 | Sutton et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh |
| 2015/0012085 A1 | 1/2015 | Salahieh et al. |
| 2015/0073540 A1 | 3/2015 | Salahieh et al. |
| 2015/0073541 A1 | 3/2015 | Salahieh et al. |
| 2015/0127094 A1 | 5/2015 | Salahieh et al. |

FOREIGN PATENT DOCUMENTS

| | | |
|---|---|---|
| WO | 2006009690 A1 | 1/2006 |
| WO | 2005062980 A3 | 5/2006 |
| WO | 2006138391 A2 | 12/2006 |
| WO | 2007033093 A2 | 3/2007 |
| WO | 2007035471 A2 | 3/2007 |
| WO | 2006138391 A9 | 4/2007 |
| WO | 2007044285 A2 | 4/2007 |
| WO | 2006138391 A3 | 5/2007 |
| WO | 2007053243 A2 | 5/2007 |
| WO | 2007058847 A2 | 5/2007 |
| WO | 2007035471 A3 | 6/2007 |
| WO | 2007092354 A2 | 8/2007 |
| WO | 2007097983 A2 | 8/2007 |
| WO | 2007053243 A3 | 9/2007 |
| WO | 2007092354 A3 | 12/2007 |
| WO | 2007033093 A3 | 1/2008 |
| WO | 2007097983 A3 | 3/2008 |
| WO | 2007058847 A3 | 4/2009 |
| WO | 2007044285 A3 | 5/2009 |
| WO | 2010042950 A2 | 4/2010 |
| WO | 2010042950 A3 | 7/2010 |

* cited by examiner

V-CLIP POST WITH PIVOTING

CROSS-REFERENCE TO RELATED APPLICATIONS

This application claims the benefit of U.S. Provisional Application No. 62/204,067, filed Aug. 12, 2015.

TECHNICAL FIELD

The present disclosure pertains to medical devices, and methods for manufacturing and/or using medical devices. More particularly, the present disclosure pertains to locking mechanisms for a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a replacement heart valve locking mechanism may comprise a buckle member fixedly attached to a tubular anchor member, a post member axially translatable relative to the buckle member, and an actuator member including a pivot pin proximate a distal end thereof. The actuator member may be releasably connected to a proximal end of the post member at the pivot pin. The post member may include a latch portion configured to engage the buckle member such that movement of the post member distally relative to the buckle member is prevented.

In addition or alternatively, and in a second aspect, the buckle member includes a protrusion configured to release the actuator member from the post member.

In addition or alternatively, and in a third aspect, the post member includes two arms spaced apart by a longitudinally-oriented slot, the two arms being configured to releasably engage the actuator member.

In addition or alternatively, and in a fourth aspect, the longitudinally-oriented slot narrows distally.

In addition or alternatively, and in a fifth aspect, the protrusion is configured to splay apart the two arms as the post member is translated proximally.

In addition or alternatively, and in a sixth aspect, the post member includes a cantilevered leg extending proximally from a distal end of the post member.

In addition or alternatively, and in a seventh aspect, the buckle member is substantially rigid.

In addition or alternatively, and in an eighth aspect, the actuator member is pivotable relative to the post member at the pivot pin.

In addition or alternatively, and in a ninth aspect, the latch portion is configured to be deflected by the buckle member as the post member is translated proximally through the buckle member.

In addition or alternatively, and in a tenth aspect, the pivot pin is rigid.

In addition or alternatively, and in an eleventh aspect, a replacement heart valve may comprise a tubular anchor member actuatable between an elongated delivery configuration and an expanded deployed configuration, a buckle member fixedly attached to the anchor member, a post member axially translatable relative to the buckle member, the post member including a latch portion configured to engage the buckle member when the anchor member is in the deployed configuration, an actuator member including a pivot pin proximate a distal end thereof, the actuator member being releasably connected to a proximal end of the post member at the pivot pin, and a valve leaflet attached to the post member. The post member may be disposed distal of the anchor member when the anchor member is in the elongated delivery configuration.

In addition or alternatively, and in a twelfth aspect, the latch portion is configured to engage the buckle member such that movement of the post member distally relative to the buckle member is prevented.

In addition or alternatively, and in a thirteenth aspect, the post member includes two arms spaced apart by a longitudinally-oriented slot, the two arms being configured to releasably engage the actuator member.

In addition or alternatively, and in a fourteenth aspect, the longitudinally-oriented slot narrows distally.

In addition or alternatively, and in a fifteenth aspect, the buckle member includes a protrusion configured to release the actuator member from the post member.

In addition or alternatively, and in a sixteenth aspect, the protrusion is configured to splay apart the two arms as the post member is translated proximally.

In addition or alternatively, and in a seventeenth aspect, the post member includes a cantilevered leg extending proximally from a distal end of the post member and the valve leaflet is attached to the cantilevered leg.

In addition or alternatively, and in an eighteenth aspect, the actuator member includes a flattened body portion configured to axially translate through the buckle member.

In addition or alternatively, and in a nineteenth aspect, the flattened body portion prevents relative rotation between the actuator member and the buckle member.

In addition or alternatively, and in a twentieth aspect, the latch portion is configured to be deflected by the buckle member as the post member is translated proximally through the buckle member.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
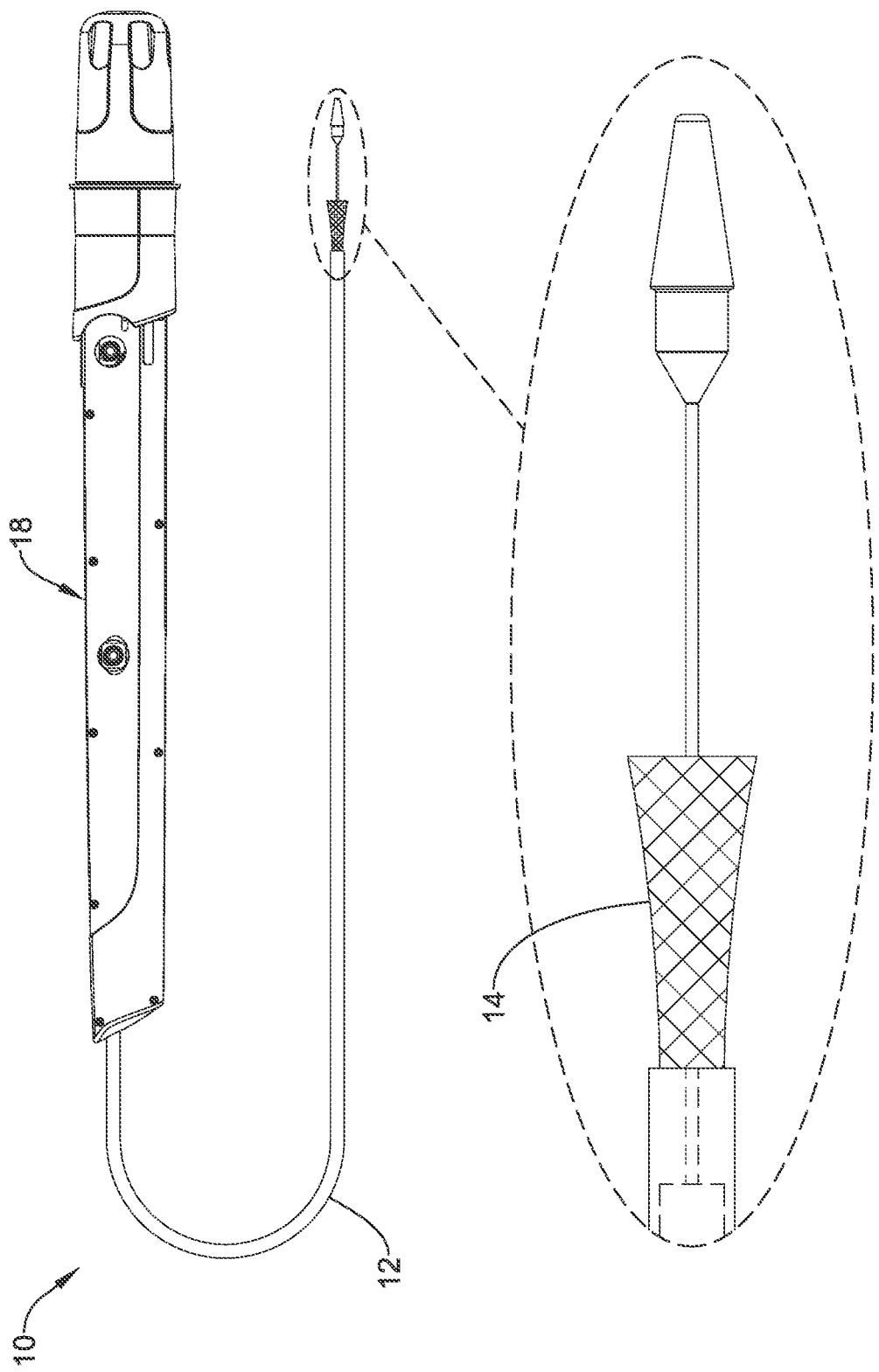
FIG. 1 illustrates an example medical implant system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

FIG. 1 illustrates a portion of an example medical implant system 10. It should be noted that some features of the medical implant system 10 are either not shown, or are shown schematically, in FIG. 1 for simplicity. Additional details regarding some of the components of the medical implant system 10 may be provided in other figures in greater detail. A medical implant system 10 may be used to deliver and/or deploy a variety of medical devices to a number of locations within the anatomy. In at least some embodiments, the medical implant system 10 may be a replacement heart valve system (e.g., a replacement aortic valve system) that can be used for percutaneous delivery of a replacement heart valve. This, however, is not intended to be limiting as the medical implant system 10 may also be used for other interventions including mitral valve replacement, valve repair, valvuloplasty, and the like, or other similar interventions.

The medical implant system 10 may generally be described as a catheter system that includes a delivery system 12 and a medical implant 14 (i.e., a replacement heart valve, for example, which term may be used interchangeably with the term "medical implant" herein) which may be coupled to the delivery system 12 and disposed within a lumen of the delivery system 12 during delivery of the medical implant 14. In some embodiments, a handle 18 may be disposed at a proximal end of the delivery system 12, and may include one or more actuation means associated therewith. In general, the handle 18 may be configured to manipulate the position of the delivery system 12 and/or aid in the deployment of the medical implant 14.

Figure 2:
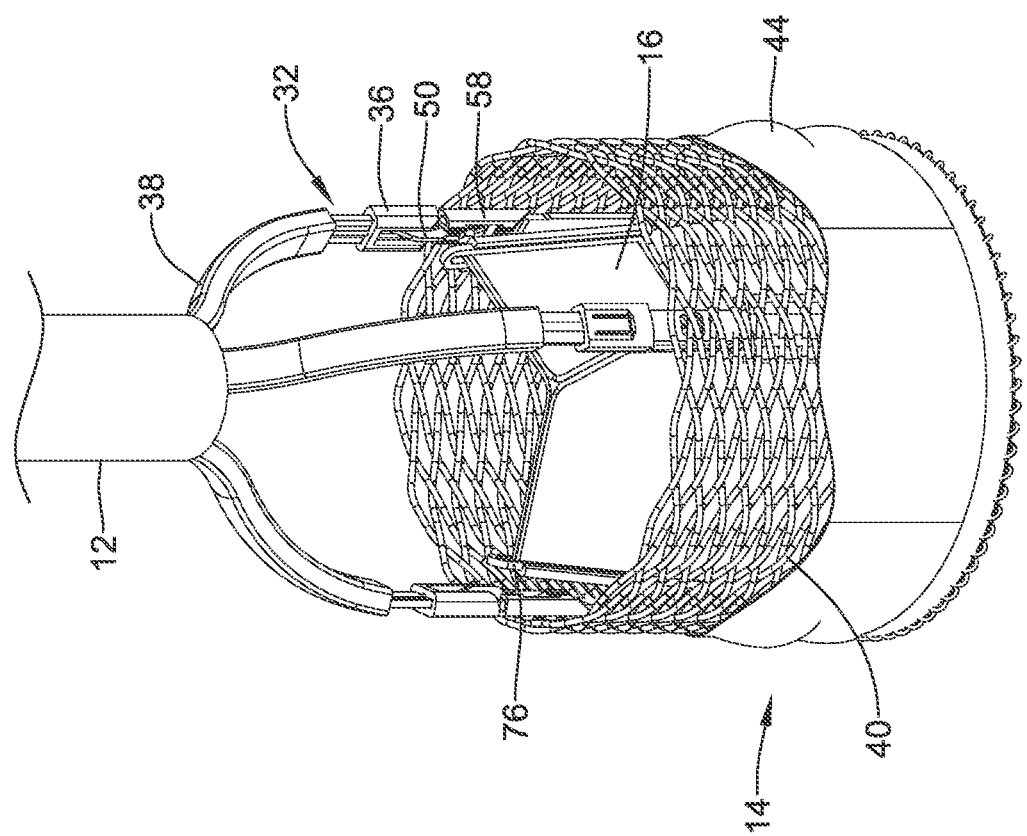
FIG. 2 illustrates an example medical implant in a deployed configuration.
Figure 3:
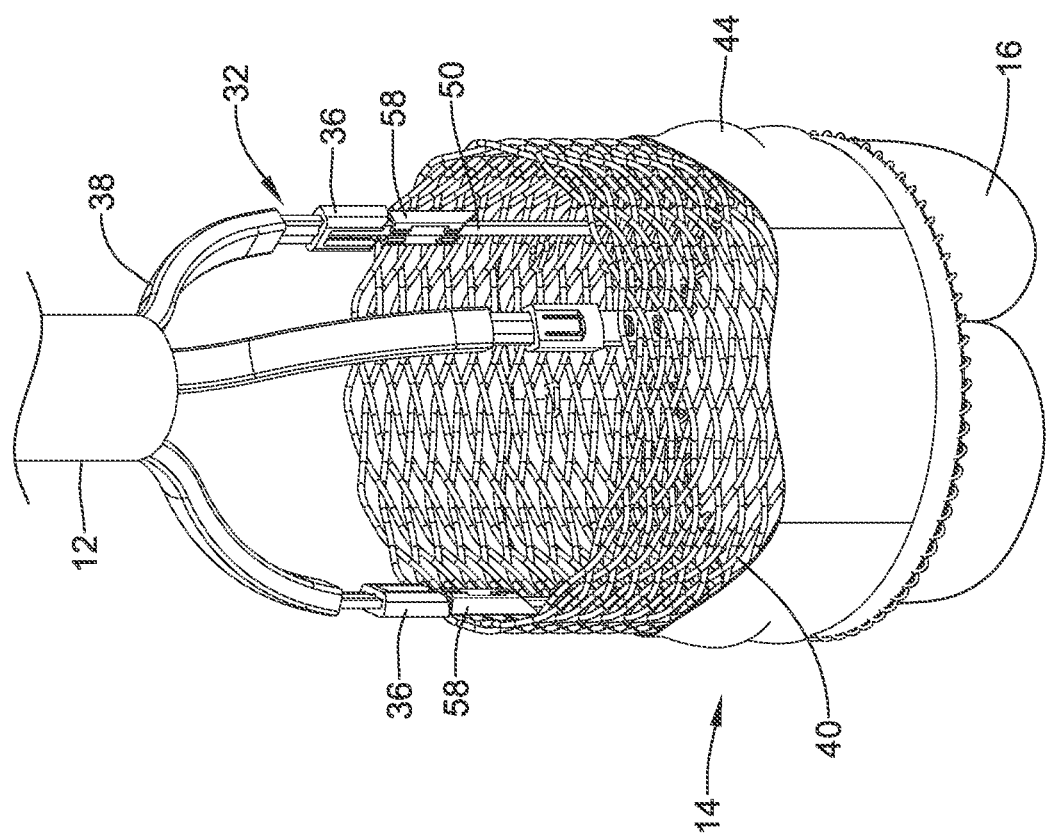
FIG. 3 illustrates an example medical implant in an everted configuration.

In use, the medical implant system 10 may be advanced percutaneously through the vasculature to a position adjacent to an area of interest. For example, the medical implant system 10 may be advanced through the vasculature and across the aortic arch to a position adjacent to a defective aortic valve. Alternative approaches to treat a defective aortic valve or other heart valve(s) are also contemplated with the medical implant system 10. During delivery, the medical implant 14 may be generally disposed in an elongated and low profile "delivery" configuration within the delivery system 12. Once positioned, the delivery system 12 may be retracted relative to the medical implant 14 to expose the medical implant 14. In at least some embodiments, the medical implant 14 may be disposed in an "everted" configuration or a partially-everted configuration, as seen in FIG. 3, for example, while disposed within the delivery system 12 and/or immediately upon exposure after retracting the delivery system 12. In some embodiments, the "delivery" configuration and the "everted" configuration may be substantially similar and/or may be used interchangeably herein. The medical implant 14 may be actuated using the handle 18 in order to translate the medical implant 14 into a generally shortened and larger profile "deployed" configuration suitable for implantation within the anatomy (as shown in FIG. 2, for example). When the medical implant 14 is suitably deployed within the anatomy, the delivery system 12 can be disconnected from the medical implant 14 and the delivery system 12 removed from the vasculature, leaving the medical implant 14 in place in a "released" configuration to function as, for example, a suitable replacement for the native aortic valve. In at least some interventions, the medical implant 14 may be deployed within the native valve (e.g., the native valve is left in place and not excised). Alternatively, the native valve may be removed and the medical implant 14 may be deployed in its place as a replacement.

In some embodiments, the delivery system 12 may include one or more lumens extending therethrough. For example, in some embodiments, the delivery system 12 may include a first lumen, a second lumen, a third lumen, and a fourth lumen. In general, the one or more lumens extend along an entire length of the delivery system 12. Other embodiments are contemplated, however, where one or more of the one or more lumens extend along only a portion of the length of the delivery system 12. For example, in some embodiments, the fourth lumen may stop just short of a distal end of the delivery system 12 and/or be filled in at its distal end to effectively end the fourth lumen proximal of the distal end of the delivery system 12.

Disposed within a first lumen of the delivery system 12 may be at least one actuator member, such as an actuator member 50 for example, which may be used to actuate (i.e., expand and/or elongate) the medical implant 14 between a delivery configuration and a deployed configuration. In some cases, the actuator member(s) 50 may herein be referred to, or used interchangeably with, the term "actuator element". In some embodiments, the medical implant system 10 may include at least one actuator member 50. In some embodiments, the at least one actuator member 50 may include a plurality of actuator members 50, two actuator members 50, three actuator members 50, four actuator members 50, or another suitable or desired number of actuator members 50. For the purpose of illustration only, the medical implant system 10 and/or the medical implant 14 is shown with three actuator members 50.

In at least some embodiments, the first lumen may be lined with a low friction liner (e.g., a FEP liner). In some embodiments, disposed within a second lumen may be at least one release pin, although dedicated release pins are not strictly necessary in every embodiment. In at least some embodiments, the second lumen may be lined with a hypotube liner. A third lumen may be a guidewire lumen and in some embodiments, the third lumen may also be lined with a hypotube liner. In some embodiments, a fourth lumen may be used to house a non-stretch wire or other reinforcing member. The form of the non-stretch wire or other reinforcing member may vary. In some embodiments, the non-stretch wire may take the form of a stainless steel braid. The non-stretch wire may optionally include a pair of longitudinally-extending aramid and/or para aramid strands (for example, KEVLAR®) disposed on opposite sides of the braid. In general, rather than being "disposed within" the fourth lumen, the non-stretch wire may be embedded within the fourth lumen. In addition, the non-stretch wire may extend to a position adjacent to a distal end region but not fully to the distal end of the delivery system 12. For example, a short distal segment of the fourth lumen may be filled in with polymer material adjacent to the distal end of the delivery system 12.

The delivery system 12 may also include a guidewire tube extension that extends distally from the distal end region. In some embodiments, a nose cone may be attached to the guidewire tube extension. In some embodiments, the nose cone generally is designed to have an atraumatic shape. In some embodiments, the nose cone may also include a ridge or ledge that is configured to abut the distal tip of the delivery system 12 during delivery of the medical implant 14.

FIGS. 2-3 illustrate some selected components of the medical implant system 10 and/or the medical implant 14 in the deployed and/or everted configuration. For example, here it can be seen that the medical implant 14 may include a plurality of valve leaflets 16 (e.g., bovine pericardial) which may be secured to a tubular anchor member or braid 40 that is reversibly actuatable between a "delivery" and/or "everted" configuration, and a "deployed" configuration. In some embodiments, the anchor member or braid 40 may be substantially cylindrical in shape or configuration. In some embodiments, the anchor member or braid 40 may define a central longitudinal axis extending therethrough along a fluid flow path through the medical implant 14. Other shapes and/or configurations are also contemplated. Some suitable but non-limiting materials for the anchor member or braid 40, for example metallic materials or polymeric materials, may be described below.

In some embodiments, the medical implant 14 may include a plurality of locking mechanisms configured to secure the anchor member or braid 40 in the "deployed" configuration. In some embodiments, the at least one actuator member 50 may be configured to engage with the plurality of locking mechanisms and actuate the anchor member or braid 40 between the "delivery" configuration and/or the "everted" configuration, and the "deployed" configuration. In some embodiments, one actuator member 50 may correspond to, engage with, and/or actuate one locking mechanism. In some embodiments, one actuator member 50 may correspond to, engage with, and/or actuate more than one locking mechanism. Other configurations are also contemplated.

FIGS. 4-11 illustrate the general relationship and operation of selected components of a locking mechanism configured to lock the medical implant 14 (and/or the anchor member or braid 40) in the "deployed" configuration. For simplicity and clarity purposes, not all elements of the disclosed invention are necessarily shown in each figure. In some illustrative examples, only one of the fingers 34 of the coupler 32, only one of the plurality of actuator members 50, only one of the post members 76, only one of the buckle members 58, and only one of the collars 36, are shown and discussed (the whole medical implant 14 and/or the anchor member or braid 40 is not shown to facilitate understanding of the locking mechanisms). However, it will be understood that the following discussion may apply equally to any and/or all of the components for which there are more than one within the medical implant 14 (i.e., the plurality of actuator members 50, the buckle members 58, the post members 76, etc.) and/or the medical implant system 10.

As seen in FIG. 2, and discussed in more detail below, each actuator member 50 extends through a guide 38 adjacent to and covering a finger 34 of the coupler 32, through a collar 36 coupling and/or locking the finger 34 to a buckle member 58, through the buckle member 58, and connected to a proximal end of a post member 76.

While a plurality of actuator members 50, post members 76, other elements, and/or corresponding locking mechanisms may be included in a medical implant 14, for clarity and brevity, much of the following discussion will be limited to a single instance of these elements. The skilled person will readily recognize that the features and operation of the examples discussed below may apply equally to and across all instances of the disclosed elements (i.e., each locking mechanism, each actuator member 50, each post member 76, etc.). Some suitable but non-limiting materials for locking mechanisms, the actuator members 50, the post members 76, etc., for example metallic materials or polymeric materials, may be described below.

In some embodiments, the plurality of locking mechanisms may each comprise an axially movable post member 76, for example at the commissure portions of the valve leaflets 16 (post member 76 may sometimes be referred to as a "commissure post", which may serve to secure the valve leaflets 16), and a buckle member 58 fixedly attached to the anchor member or braid 40. In other words, in at least some embodiments, a medical implant 14 may include a plurality of post members 76 and a corresponding plurality of buckle members 58. Other configurations and correspondences are also contemplated.

In some embodiments, the post member 76 may engage the buckle member 58 in the "deployed" configuration, and consequently, in the "released" configuration. In some embodiments, the post member 76 may be axially and/or longitudinally spaced apart from the buckle member 58 in the "delivery" configuration and/or the "everted" configuration. Some suitable but non-limiting materials for the post member 76 and/or the buckle member 58, for example metallic materials or polymeric materials, may be described below.

In some embodiments, a distal end of the axially movable post member 76 may be secured and/or attached (i.e., fixedly attached, movably attached, removably attached, etc.) to a distal portion of the anchor member or braid 40, such as by a suture 74, a tether, adhesives, or other suitable element. In some embodiments, the post member 76 may be movable relative to the anchor member or braid 40, and the buckle member 58. In some embodiments, the post member 76 may be axially or longitudinally movable relative to the anchor member or braid 40, and the buckle member 58. In some embodiments, the buckle member 58 may be fixedly attached to the anchor member or braid 40. Other embodiments are contemplated where the buckle member 58 may be movably or removably attached to the anchor member or braid 40. In some embodiments, the post member 76 may be fixedly attached to the anchor member or braid 40 and the buckle member 58 may be fixedly attached to the anchor member or braid 40. In some embodiments, one of the post member 76 and the buckle member 58 may be fixedly attached to the anchor member or braid 40 and the other may be movably or removably attached to the anchor member or braid 40. In some embodiments, the post member 76 may be movably or removably attached to the anchor member or braid 40 and the buckle member 58 may be movably or removably attached to the anchor member or braid 40. In some embodiments, the post member 76 may be secured or attached (i.e., fixedly attached, movably attached, removably attached, etc.) to a distal end of the anchor member or braid 40. In some embodiments, the buckle member 58 may be fixed or attached to a proximal portion of the anchor member or braid 40. In some embodiments, the buckle member 58 may be fixed or attached at or to a proximal end of the anchor member or braid 40.

In some embodiments, the medical implant 14 may include one or more of the plurality of valve leaflets 16 secured to the anchor member or braid 40 at, adjacent to, and/or using (at least in part) individual, corresponding post members 76. In some embodiments, the plurality of valve leaflets 16 may also be secured to a base, or the distal end, of the anchor member or braid 40. As such, when the post member 76 is pulled proximally to engage the buckle member 58, as will be described herein, the distal end of the anchor member or braid 40 is also pulled proximally relative to the buckle member 58, thereby transitioning from the "delivery" configuration and/or the "everted" configuration toward the "deployed" configuration. In some embodiments, the plurality of valve leaflets 16 may be coupled and/or secured (i.e., to the post member 76, to the anchor member or braid 40, and/or back to themselves) using one or more sutures, threads, wires, filaments, or other suitable elements. In some embodiments, the plurality of valve leaflets 16 may be coupled and/or secured (i.e., to the post member 76, to the anchor member or braid 40, and/or back to themselves) using an adhesive, a bonding agent, or other suitable securing means. In some embodiments, the plurality of valve leaflets 16 may be coupled and/or secured (i.e., to the post member 76, to the anchor member or braid 40, and/or back to themselves) using a fabric, a textile, or other thin flexible material.

In some embodiments, the anchor member or braid 40 may have a total of three buckle members 58 and three post members 76 attached and/or secured thereto. Similarly, one actuator member 50 may be operatively associated with each post member 76 and buckle member 58, for a total of three actuator members 50 in the illustrated examples. Other embodiments are contemplated where fewer or more buckle members 58, post members 76, actuator members 50, etc. may be utilized. In some embodiments, a seal 44 may be disposed about the anchor member or braid 40 and, as the term suggests, may help to seal an exterior of the medical implant 14 within and/or against a target site or area of interest upon deployment, thereby preventing leakage around the medical implant 14.

In some embodiments, attachment between the medical implant 14 and the delivery system 12 may be effected through the use of a coupler 32. In some embodiments, the coupler 32 may generally include a cylindrical base (not shown) that may be disposed about, attached to, and/or extending from the delivery system 12. Projecting distally from the base is a plurality of fingers 34 (e.g., two, three, four, etc.) that are each configured to engage with the medical implant 14 at a proximal end of one of the buckle members 58. A collar 36 may be disposed about each of the fingers 34 of the coupler 32 to further assist in holding together the fingers 34 and the buckle members 58, as will be described in more detail below. A guide 38 may be disposed over each of the fingers 34 proximal of the collar 36 and may serve to keep the fingers 34 of the coupler 32 associated with the plurality of actuator members 50 extending adjacent to (and axially slidable relative to) the fingers 34 of the coupler 32. Finally, a pivot pin 20 may be a linking structure that keeps the post member 76, the buckle member 58, and the actuator member 50 associated with one another. In some embodiments, the pivot pin 20 may be fixedly attached and/or secured to a distal end of the actuator member 50. In some embodiments, the pivot pin 20 may be integrally formed with or as a single monolithic structure with the actuator member 50. In some embodiments, the pivot pin 20 may include a plurality of pin members each fixedly attached and/or secured to the distal end of the actuator member 50. Some suitable but non-limiting materials for the coupler 32, the plurality of fingers 34, the collar 36, the guide 38, and/or the pivot pin 20, for example metallic materials or polymeric materials, may be described below.

In some embodiments, a buckle member 58 may include a proximal end and a distal end disposed opposite the proximal end. In some embodiments, the buckle member 58 may include a back wall extending from the proximal end to the distal end. In some embodiments, the buckle member 58 may include two axially-extending side walls extending radially inward toward the central longitudinal axis away from the back wall and/or the anchor member or braid 40, when the buckle member 58 is attached thereto. In some embodiments, the back wall may be configured to matingly engage a radially inner surface of the anchor member or braid 40, such that the back wall is disposed radially distant from the central longitudinal axis of the medical implant 14 relative to the two side walls. In some embodiments, the back wall may include a generally planar inner surface facing toward the central longitudinal axis when the buckle member 58 is fixedly attached and/or secured to the anchor member or braid 40. In some embodiments, the back wall may include a curved outer surface configured to mate with and/or lie against an inner surface of the tubular anchor member or braid 40 when the buckle member 58 is fixedly attached and/or secured to the anchor member or braid 40.

In some embodiments, the two axially-extending side walls may include a first side wall and a second side wall. In some embodiments, each side wall may include an upper flange extending from a top of the side wall distant from the back wall, the upper flange extending inwardly toward a central plane through the buckle member 58 (and/or the central longitudinal axis) normal to the back wall. In at least some embodiments, the upper flange(s) may be oriented generally parallel to the back wall and/or an inside surface of the back wall.

In some embodiments, the back wall may extend between the two side walls, such that the two side walls, the back wall, and/or the upper flange(s) define a channel extending axially through the buckle member 58. In some embodiments, the buckle member 58 and/or the channel may include a suitable shape and/or keying feature(s) configured to cooperate with the actuator member 50 to prevent relative rotation between the actuator member 50 and the buckle member 58. In some embodiments, the back wall may include one or more apertures disposed within the back wall and between the two side walls. In some embodiments, a fastening element (e.g., a suture, thread, wire, filament, etc.) may pass through the one or more apertures and secure the buckle member 58 to the anchor member or braid 40. In some embodiments, the back wall may include a recessed portion in communication with some or all of the one or more apertures and/or the distal end of the buckle member 58. In some embodiments, the fastening element may extend away from the buckle member 58 through the recessed portion when the post member 76 is disposed within the channel.

Figure 7:
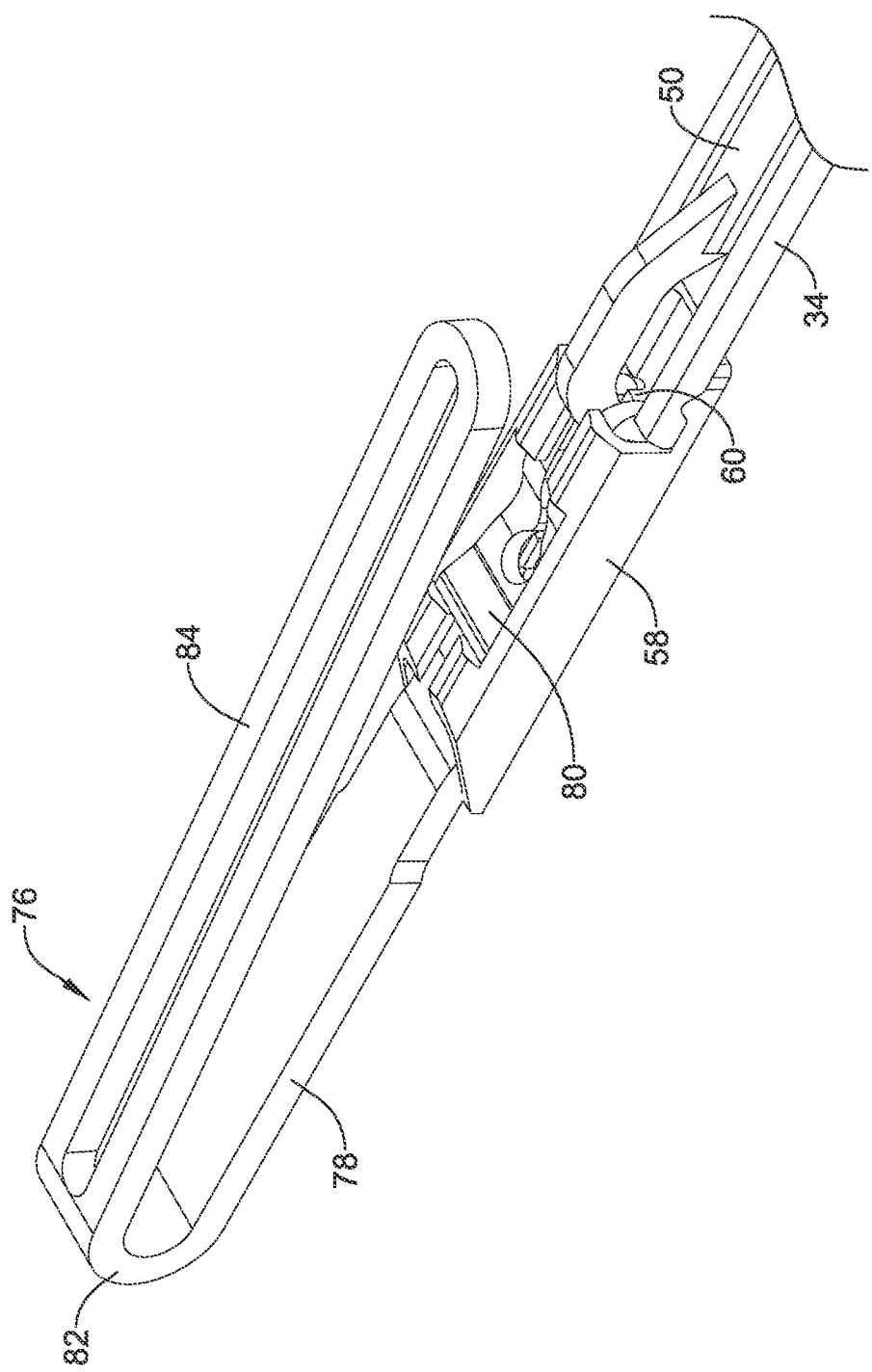
FIG. 7 is a perspective view of selected components of an example locking mechanism associated with an example medical implant.
Figure 11:
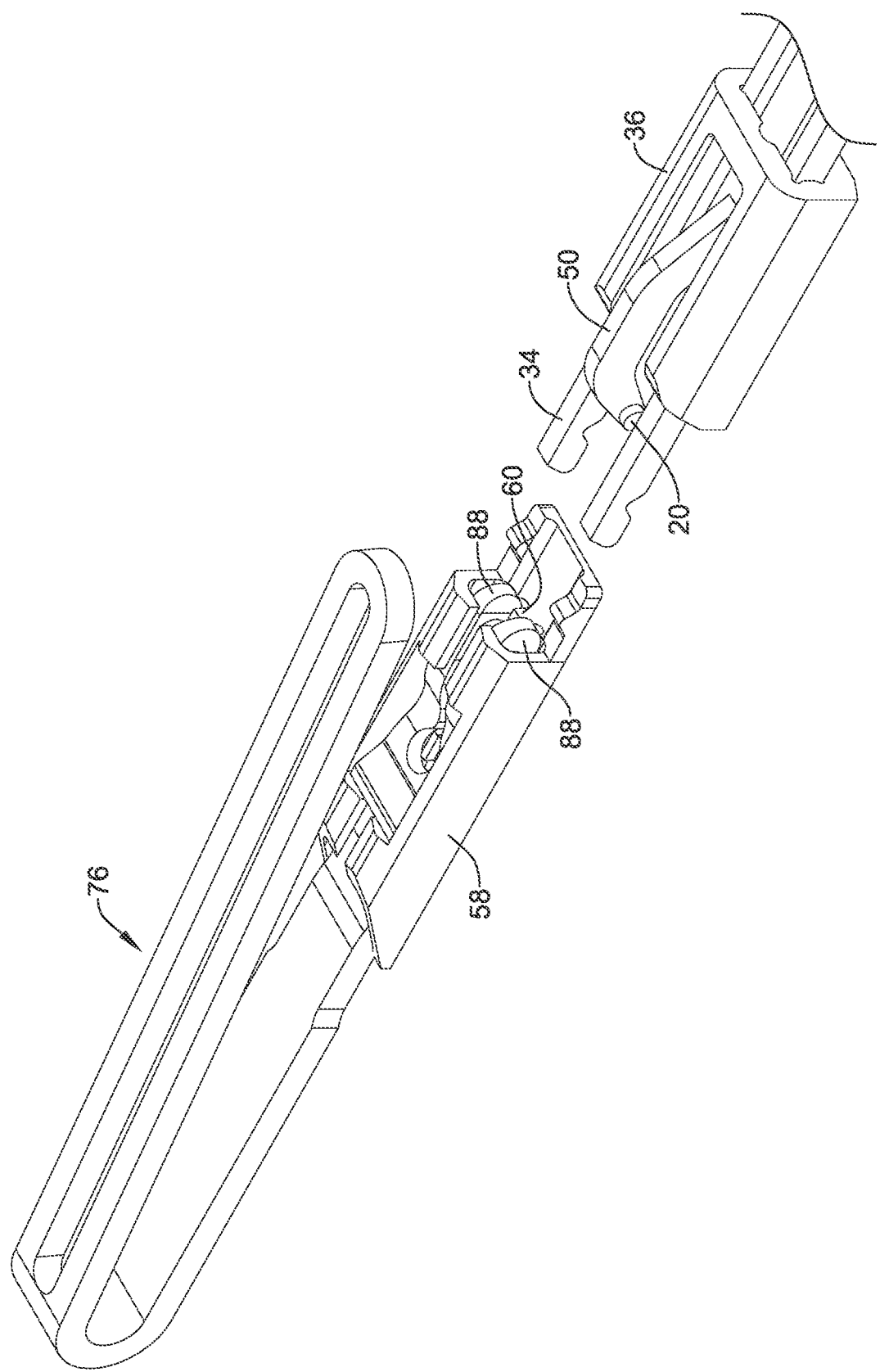
FIG. 11 illustrates selected components of an example locking mechanism associated with an example medical implant in a released configuration.

In some embodiments, the buckle member 58 may include a longitudinally-oriented protrusion 60 extending radially inward toward the central longitudinal axis from the back wall of the buckle member 58, for example along the central plane, as seen in FIGS. 7 and 11 for example. In at least some embodiments, the longitudinally-oriented protrusion 60 may be integrally formed with and/or as a part of the buckle member 58. In some embodiments, the longitudinally-oriented protrusion 60 may extend across less than half of the channel extending axially through the buckle member 58. In some embodiments, the longitudinally-oriented protrusion 60 may cooperate with the upper flange(s) to guide and/or orient the actuator member 50 disposed therebetween. In some embodiments, the longitudinally-oriented protrusion 60 may be configured to release the actuator member 50 from the post member 76. In some embodiments, the longitudinally-oriented protrusion 60 may engage with the two arms 88 of the post member 76, as will be described further herein, when the post member 76 is engaged with the buckle member 58. In some embodiments, proximal translation of the actuator member 50 and the post member 76 such that the two arms 88 engage with the longitudinally-oriented protrusion 60 may cause the longitudinally-oriented protrusion 60 to splay apart the two arms 88 as the actuator member 50 and the post member 76 are translated proximally.

In some embodiments, the buckle member 58 may be substantially rigid. In some embodiments, the buckle member 58 may be formed from a metallic material, a polymeric material, a ceramic material, a composite material, or other suitable materials or combinations thereof. In some embodiments, the buckle member 58 may be partially rigid and/or partially flexible. In some embodiments, a buckle member 58 may permit an actuator member 50 and/or a post member 76 to be slidably received within and/or axially translate axially through the channel. In some embodiments, the buckle member 58 may be configured to prevent the actuator member 50 and/or the post member 76 from exiting the buckle member 58 in a radially inward direction toward the central longitudinal axis of the anchor member or braid 40, thereby limiting motion of the actuator member 50 and/or the post member 76 within the anchor member or braid 40 to axial translation.

In some embodiments, an example post member 76 may include a proximal end and a distal end. In some embodiments, the post member 76 may include a body portion 78 extending generally along a first plane. In some embodiments, when the post member 76 is engaged with the buckle member 58, the first plane may be oriented generally parallel to an inside surface of the back wall of the buckle member 58. In some embodiments, the post member 76 may include a latch portion 80 connected to and/or integrally formed with or as a part of the body portion 78. In some embodiments, the latch portion 80 may extend laterally away from and/or may be laterally offset from the body portion 78 and/or the first plane. In some embodiments, the latch portion 80 may be resilient and/or self-biased away from the body portion 78 and/or the first plane. In some embodiments, the latch portion 80 may be configured to be deflected by the buckle member 58 as the post member 76 is translated proximally through the buckle member 58. In some embodiments, the post member 76 may be reversibly actuatable between a first orientation, wherein the proximal end and/or the latch portion 80 extends distally from the body portion 78 (e.g., in the "delivery" and/or "everted" configuration), and a second orientation, wherein the proximal end and/or the latch portion 80 extend proximally from the body portion 78. In some embodiments, the post member 76 may be axially translatable relative to the buckle member 58.

In some embodiments, the post member 76 may include a cantilevered leg 84 connected by a flexible hinge portion 82 at the distal end of the post member 76. In some embodiments, the cantilevered leg 84 may extend proximally from the hinge portion 82 and/or the distal end to a free end of the cantilevered leg 84 disposed radially inward from the body portion 78 and/or the latch portion 80 (relative to the anchor member or braid 40), when the post member is in the second orientation. In some embodiments, the free end may be disposed proximal of the latch portion 80 when the post member is in the second orientation. In some embodiments, the latch portion 80 may be disposed proximal of the distal end and/or the hinge portion 82 when the post member is in the second orientation.

In some embodiments, the hinge portion 82 may have and/or include a radius of curvature. For example, in some embodiments, the radius of curvature may be between 0 and 3 millimeters (mm). In some embodiments, the radius of curvature may be an inner radius of curvature of between 0 and 3 millimeters (mm). In some embodiments, the radius of curvature may be an outer radius of curvature of between 0 and 3 millimeters (mm). Other configurations and radii of curvature are also contemplated. In some embodiments, the hinge portion 82 may be configured to dispose the body portion 78 and the cantilevered leg 84 at an acute angle relative to each other. In some embodiments, the acute angle may be between about 0 degrees and about 90 degrees, between about 3 degrees and about 60 degrees, between about 5 degrees and about 45 degrees, between about 8 degrees and about 30 degrees, between about 10 degrees and about 20 degrees, between about 12 degrees and about 16 degrees, about 14 degrees, or another suitable angle. In at least some embodiments, the hinge portion 82 flexibly attaches the cantilevered leg 84 to the body portion 78 of the post member 76. In some embodiments, at least part of the cantilevered leg 84 may longitudinally overlap the buckle member 58 along a central longitudinal axis of the anchor member or braid 40 in the "deployed" configuration.

In some embodiments, the cantilevered leg 84 may include a free end and a secured end, where the cantilevered leg 84 may be attached to the body portion 78 of the post member 76 at the secured end, which may connect directly to the hinge portion 82. In some embodiments, the free end of the cantilevered leg 84 may be unattached (i.e., not directly attached) to any other structure of the medical implant 14, except for the cantilevered leg 84 and/or the plurality of valve leaflets 16. In other words, in some embodiments, the free end may not be directly attached to any other structure or feature of the medical implant 14 (i.e., the buckle member 58, the anchor member or braid 40, etc.). In some embodiments, a distalmost end of the post member 76, which in at least some embodiments may be and/or include the hinge portion 82, may be coupled to the distal end of the anchor member or braid 40, such as, for example, by a fastening element such as a suture 74, a filament, a wire, or other suitable means. In some embodiments, the body portion 78 may include one or more apertures or holes for securing the post member 76 to the anchor member or braid 40 using a fastening element, such as a suture, for example. As such, when the post member 76 is pulled proximally to engage the buckle member 58, the distal end of the anchor member or braid 40 is also pulled proximally relative to the buckle member 58, thereby transitioning from the "delivery" configuration toward the "deployed" configuration.

In at least some embodiments, one or more of the plurality of valve leaflets 16 may be attached to the cantilevered leg(s) 84. In some embodiments, attachment of the plurality of valve leaflets 16 to the cantilevered leg(s) 84 may provide flexibility and/or a reduction in stress between the plurality of valve leaflets 16 and the anchor member or braid 40. In some embodiments, at least a portion of the plurality of valve leaflets 16 may axially or longitudinally overlap at least a portion of the buckle members 58 at a common position along a central longitudinal axis of the anchor member or braid 40, which in some embodiments may allow for a shorter overall length or height of the medical implant 14. In some embodiments, the plurality of valve leaflets 16 may be secured directly to the cantilevered leg(s) 84. In some embodiments, the plurality of valve leaflets 16 may not be directly secured to the body portion 78 of the post member 76, but is instead coupled to the post member 76 via the cantilevered leg(s) 84. In some embodiments, the plurality of valve leaflets 16 may be wrapped around at least a portion of the cantilevered leg(s) 84. In some embodiments, a distalmost end of the plurality of valve leaflets 16 may be coupled to the distal end of the anchor member or braid 40. In some embodiments, the plurality of valve leaflets 16 may be coupled and/or secured (i.e., to the cantilevered leg 84, to the anchor member or braid 40, and/or back to themselves) using one or more sutures, threads, wires, filaments, or other suitable elements. In some embodiments, the plurality of valve leaflets 16 may be coupled and/or secured (i.e., to the cantilevered leg 84, to the anchor member or braid 40, and/or back to themselves) using an adhesive, a bonding agent, or other suitable securing means. In some embodiments, the plurality of valve leaflets 16 may be coupled and/or secured (i.e., to the cantilevered leg 84, to the anchor member or braid 40, and/or back to themselves) using a fabric, a textile, or other thin flexible material.

Figure 10:
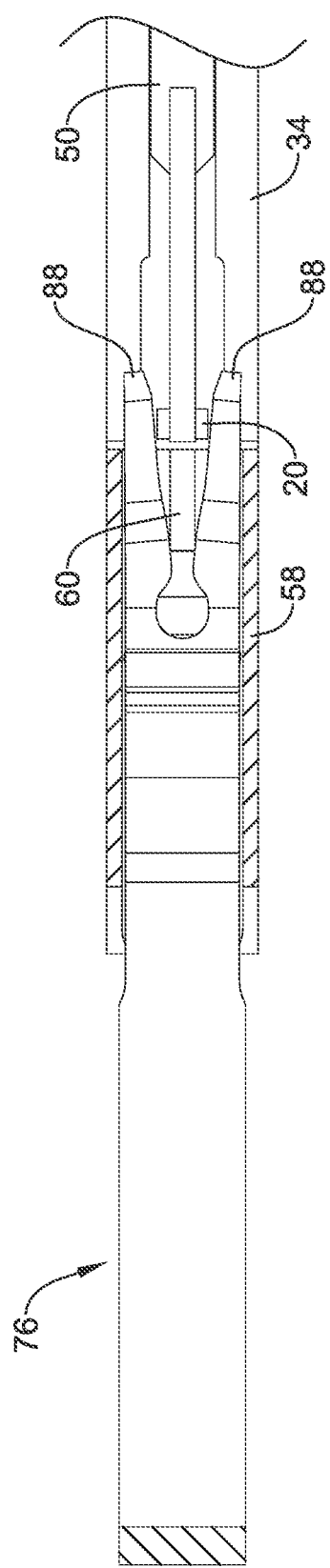
FIG. 10 illustrates selected components of an example locking mechanism associated with an example medical implant in a deployed configuration.

In some embodiments, the proximal end of the post member 76 may include two arms 88 extending proximally from the body portion 78 and/or the latch portion 80 when the post member is in the second orientation. In some embodiments, the two arms 88 may be spaced apart by a longitudinally-oriented slot. In some embodiments, the longitudinally-oriented slot may narrow distally. In some embodiments, each of the two arms 88 may include an aperture extending into and/or from the longitudinally-oriented slot such that the aperture is in communication with the longitudinally-oriented slot. In some embodiments, the aperture may extend partially through its arm 88 in a transverse and/or circumferential (with respect to the central longitudinal axis and/or the anchor member or braid 40) direction. In some embodiments, the aperture may extend completely through its arm 88 in a transverse and/or circumferential (with respect to the central longitudinal axis and/or the anchor member or braid 40) direction. In some embodiments, the two arms 88 may be configured to releasably engage the actuator member 50, thereby releasably connecting the actuator member 50 to the proximal end of the post member 76. In some embodiments, as the actuator member 50 and/or the post member 76 is translated proximally through the buckle member 58 in the second orientation, the longitudinally-oriented slot of the post member 76 may contact and/or engage the longitudinally-oriented protrusion 60. In some embodiments, the longitudinally-oriented protrusion 60 may be configured to splay apart the two spaced apart arms 88 as the post member 76 is translated proximally when the longitudinally-oriented slot contacts the longitudinally-oriented protrusion 60, as seen in FIG. 10 for example.

In some embodiments, the latch portion 80 may be configured to engage the flange(s) of the buckle member 58 when the post member is in the second orientation, such that movement of the post member 76 distally relative to the buckle member 58 is prevented. In some embodiments, the latch portion 80 may include a transversely-oriented ridge configured to engage with the flange(s) when the post member is in the second orientation. In some embodiments, at least a portion of the post member 76 is flexible. In some embodiments, the latch portion 80 may be movable relative to the body portion 78. In some embodiments, the latch portion 80 may be deflectable relative to the body portion 78 such that the latch portion 80 may translate laterally relative to the body portion 78. In some embodiments, the cantilevered leg 84 may be movable toward and away from the body portion 78 at and/or using the hinge portion 82.

In some embodiments, the body portion 78 may be unitary with and/or integrally formed with the latch portion 80, the hinge portion 82, the cantilevered leg 84, and/or the two arms 88 as and/or from a single piece of material. In some embodiments, the post member 76 may be formed from a single piece of wire, flat stock, or other suitable material as discussed herein. In some embodiments, the post member 76 may be formed by further processing the single piece of wire, flat stock, or other suitable material, such as by machining, stamping, laser cutting, etc. Some suitable but non-limiting materials for the body portion 78, the latch portion 80, the hinge portion 82, the cantilevered leg 84, and/or the two arms 88, for example metallic materials or polymeric materials, may be described below.

In some embodiments, an example actuator member 50 may include a proximal end and a distal end. In use, the proximal end may be connected to and/or manipulated or otherwise actuated by a user, for example using the handle 18, to shift the medical implant 14 from a "delivery" configuration and/or an "everted" configuration to a "deployed" configuration, and later to a "released" configuration. In some embodiments, the actuator member 50 may be axially translatable relative to the buckle member 58. In some embodiments, the actuator member 50 may be axially translatable within and/or through the channel of the buckle member 58. In some embodiments, the actuator member 50 and/or the elongated rod may slidingly mate with and/or engage a radially-inwardly facing surface of the longitudinally-oriented protrusion 60 of the buckle member 58 and/or one or both of the two side walls of the buckle member 58. In some embodiments, the radially-inwardly facing surface of the longitudinally-oriented protrusion 60 may be generally parallel to the inside surface of the back wall of the buckle member 58. In some embodiments, the radially-inwardly facing surface of the longitudinally-oriented protrusion 60 may be generally normal and/or perpendicular to an inside surface of each of the two side walls of the buckle member 58.

In some embodiments, the actuator member 50 may include an elongated rod and a distal end portion releasably connected to a proximal end and/or the two arms 88 of the post member 76. In some embodiments, the distal end portion may be integrally formed with or as a part of the elongated rod as a single monolithic structure. In some embodiments, the actuator member 50 may be prevented from rotating (i.e., is non-rotatable) relative to the buckle member 58 when the actuator member 50 is engaged with the buckle member 58. In some embodiments, the actuator member 50 may be prevented from rotating (i.e., is non-rotatable) relative to the post member 76 when the actuator member 50 is engaged with the post member 76.

In some embodiments, the distal end portion may include a pivot pin 20 fixedly attached and/or secured thereto. In some embodiments, the actuator member 50 may be aligned with and/or releasably connected to the proximal end and/or the two arms 88 of the post member 76 at the pivot pin 20. In some embodiments, the distal end portion may be slidingly received within the longitudinally-oriented slot disposed between the two arms 88 of the post member 76. In some embodiments, the pivot pin 20 may be configured to engage with, be received by, and/or extend into the aperture formed within each of the two arms 88 of the post member 76. In some embodiments, the actuator member 50 may be pivotable relative to the post member 76 at the pivot pin 20. In some embodiments, the pivot pin 20 may include a plurality of pin members each fixedly attached and/or secured to the distal end portion of the actuator member 50.

In some embodiments, the post member 76 may be pivotable relative to the actuator member 50 at the pivot pin 20 when actuating between the first orientation and the second orientation.

In some embodiments, the actuator member 50 and/or the elongated rod may be generally round, oblong, ovoid, rectangular, polygonal (i.e., two-sided, three-sided, four-sided, five-sided, six-sided, etc.) in shape. Other shapes, both regular and irregular, are also contemplated. In some embodiments, the actuator member 50 may be formed from a single piece of wire, round stock, or other suitable material, as discussed herein. In some embodiments, the actuator member 50 may be formed by further processing the single piece of wire, round stock, or other suitable material, such as by machining, stamping, laser cutting, etc. Some suitable but non-limiting materials for the actuator member 50, the elongated rod, the distal end portion, and/or the pivot pin 20, for example metallic materials or polymeric materials, may be described below.

General operation of some embodiments may be described as follows herein. During delivery, the medical implant 14 may be secured at the distal end of the delivery system 12 by virtue of the association of the fingers 34 of the coupler 32 being coupled with a projecting proximal end of the buckle member 58 (and being held in place with the collar 36 disposed over the connection) and by virtue of the pivot pin 20 securing together the actuator member 50 and the post member 76, as described herein. As can be appreciated, a proximal end of the post member 76 and a distal end of the buckle member 58 may be longitudinally separated (as seen in FIGS. 3-4, for example) and, accordingly, the medical implant 14 may be in an elongated and generally low-profile "delivery" configuration and/or "everted" configuration suitable for percutaneous translation through a patient's anatomy to an area of interest and/or target site.

After the medical implant 14 is advanced to the target site or area of interest within a distal end of the delivery system 12 in the "delivery" configuration, as seen in FIG. 1 for example, the delivery system 12 may be withdrawn or retracted to expose the medical implant 14 (or the medical implant 14 may be advanced distally relative to the delivery system 12) in the "everted" configuration, as seen in FIG. 3 for example. In the "delivery" configuration and/or the "everted" configuration, the actuator member 50 passes through the buckle member 58 and is positioned alongside the body portion 78 of the corresponding post member 76 in a generally parallel, non-inline arrangement. In the "delivery" configuration and/or the "everted" configuration, the post member 76 may be disposed in a first orientation, wherein the proximal end and/or the latch portion 80 of the post member 76 is disposed distal of the anchor member or braid 40 and/or the proximal end and/or the latch portion 80 is disposed distally of the body portion 78 of the post member 76.

Figure 4:
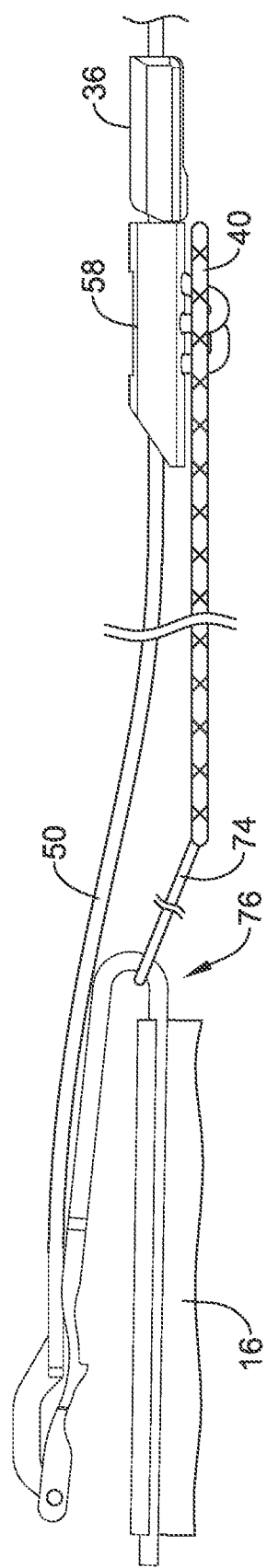
FIG. 4 illustrates selected portions of an example medical implant in an everted configuration.
Figure 5:
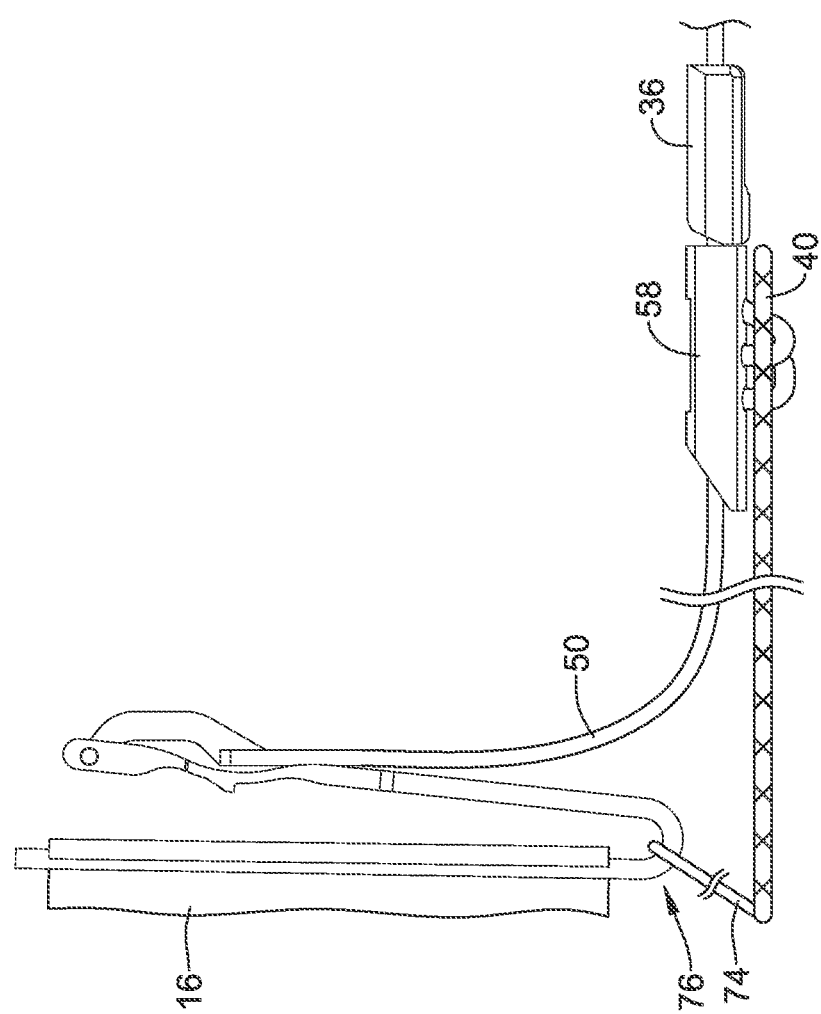
FIG. 5 illustrates selected portions of an example medical implant in a partially deployed configuration.
Figure 6:
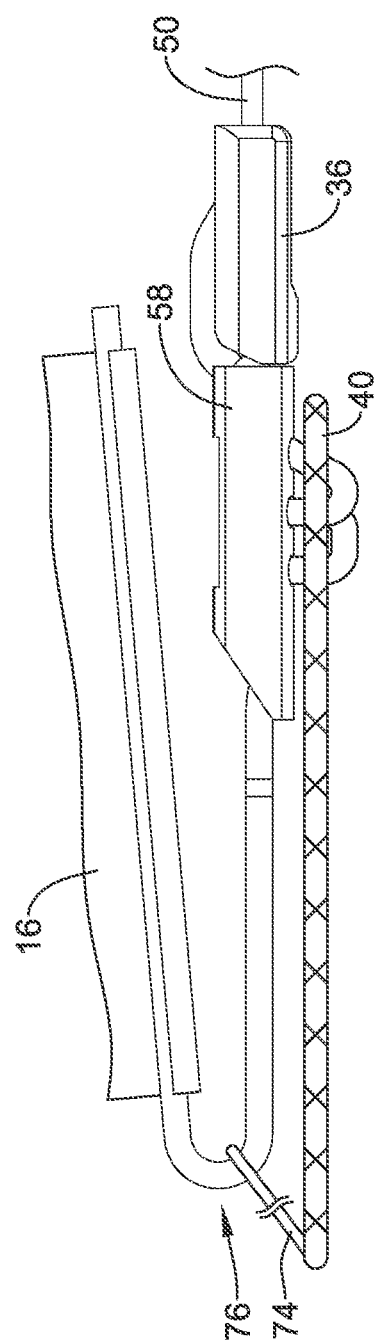
FIG. 6 illustrates selected portions of an example medical implant in a partially deployed configuration.

Then, the handle 18 and/or the plurality of actuator members 50 can be used to axially shorten and/or radially expand and "lock" the medical implant 14 and/or the anchor member or braid 40 from the "delivery" configuration and/or the "everted" configuration toward an expanded or "deployed" configuration (as shown in FIG. 2, for example) by proximally retracting the actuator member 50 through the buckle member 58, thereby causing the post member 76 to pivot relative to the actuator member 50 to rotate and/or pull the post member 76 from the first orientation through the anchor member or braid 40 and into a second orientation, wherein the proximal end and/or the latch portion 80 of the post member 76 is disposed proximally of the body portion 78 of the post member 76, and is disposed adjacent to and/or aligned with the buckle member 58, as seen in FIGS. 4-6 for example. As the post member 76 pivots and/or rotates through the anchor member or braid 40, the proximal end and/or the latch portion 80 extends toward the central longitudinal axis of the anchor member or braid 40. The actuator member 50, releasably connected to the proximal end and/or the two arms 88 of the post member 76 at the pivot pin 20, may resiliently flex radially inwardly from the buckle member 58 toward the central longitudinal axis of the anchor member or braid 40 and then back outwardly toward the anchor member or braid 40 as the proximal end and/or the latch portion 80 of the post member 76 rotates over center (i.e., flips about a distal end thereof) such that the proximal end and/or the latch portion 80 is disposed proximally of the body portion 78 of the post member 76. When the post member 76 is disposed in the second orientation, the actuator member 50 is positioned in a generally inline, end-to-end arrangement with the body portion 78 and/or the latch portion 80 of the post member 76.

Figure 8:
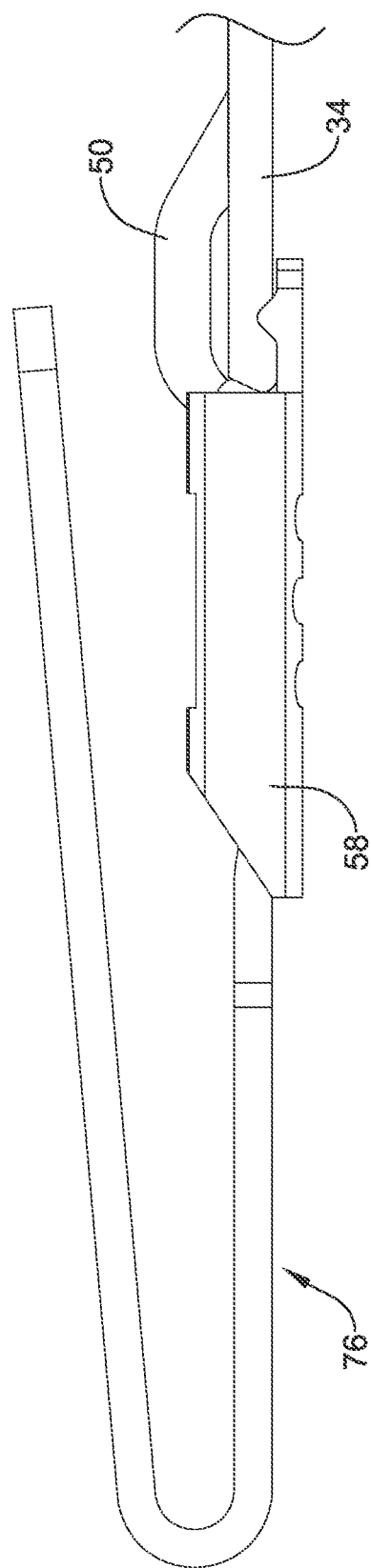
FIGS. 8-9 are alternative views of the selected components of an example locking mechanism of FIG. 7.

Further proximal retraction of the actuator member 50 brings the proximal end and/or the latch portion 80 of the post member 76 into engagement with the buckle member 58, as seen in FIGS. 6-8 for example, wherein the post member 76, when positioned within buckle member 58, is movable distally relative to the buckle member 58 as long as the latch portion 80 has not translated proximally past the flange(s) of the buckle member 58 and locked into the "deployed" configuration. In other words, the actuator member 50 and/or the post member 76 may be translated distally relative to the buckle member 58 to actuate the anchor member or braid 40 back towards the "everted" configuration, so as to permit re-placement and/or re-sheathing of the medical implant 14, up until the latch portion 80 "locks" the medical implant 14 and/or the anchor member or braid 40 into the "deployed" configuration. When the actuator member 50 is urged distally, the actuator member 50 may be translated distally relative to the buckle member 58. This distal axial translation of the actuator member 50 may cause a portion of the elongated rod, extending distally of the delivery system 12 and through the buckle member 58 to deflect and or bend radially inward toward the central longitudinal axis as the post member 76 rotates and pivots relative to the actuator member 50 from the second orientation to the first orientation.

Figure 9:
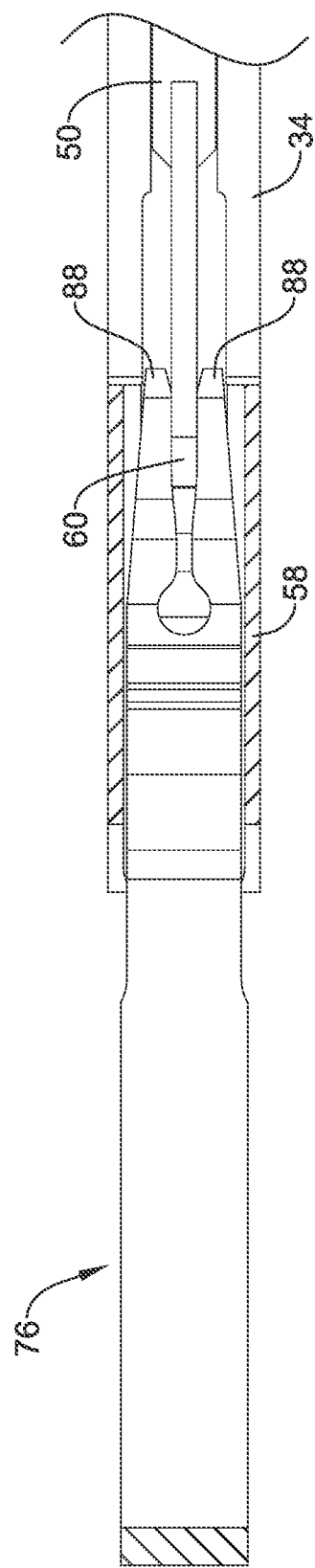

When retracting or pulling the actuator member 50 proximally, the actuator member 50 can be retracted sufficiently far enough to engage the latch portion 80 of the post member 76 with the flange(s) of the buckle member 58, thereby preventing distal movement of the post member 76 relative to the buckle member 58, such as under rebound stress from the anchor member or braid 40, so as to lock the medical implant 14 in the "deployed" configuration (as seen in FIGS. 9-10, for example), suitable for implantation within the anatomy. In other words, in some embodiments, proximal axial translation of the actuator member 50 (and therefore the post member 76 releasably connected thereto) in a proximal direction relative to the buckle member 58 may actuate the anchor member or braid 40 from the "delivery" configuration to the "deployed" configuration.

Finally, after the medical implant 14 and/or the anchor member or braid 40 has been actuated into the "deployed" configuration, as seen in FIGS. 7-9 for example, the actuator member 50 may be further translated proximally such that the two arms 88 engage opposing sides of the longitudinally-oriented protrusion 60 of the buckle member 58 and splay apart the two arms 88 to release the pivot pin 20 from the proximal end and/or the two arms 88 of the post member 76 and disconnect and/or decouple the actuator member 50 from the post member 76, as seen in FIG. 10 for example.

After the pivot pin 20 is disconnected and/or decoupled from the proximal end and/or the two arms 88 of the post member 76, further retraction of the actuator member 50 may cause the distal end portion of the actuator member 50 to engage the collar 36 and cause the collar 36 to slide proximally along the finger 34 of the coupler 32 as the actuator member 50 is retracted proximally. In doing so, a forked end, which has a groove formed therein, of the finger 34 of the coupler 32, is exposed and can be uncoupled from a rail, which has a projection formed thereon that is configured to matingly engage with the groove, on the proximal end of the buckle member 58, as shown in FIG. 11. After the forked end has disengaged from the rail, further proximal retraction of the actuator member 50 causes the finger 34 of the coupler 32 to retract proximally from the locking mechanism and the medical implant 14, thereby leaving the medical implant 14 disposed at the target site in the "released" configuration, as seen in FIG. 11 for example. Lastly, after releasing the medical implant 14 at the target site, the delivery system 12 may be re-sheathed, re-stowed, and or otherwise made ready to be removed from the patient's vasculature, and then withdrawn from the vasculature.

The materials that can be used for the various components of the medical implant system 10 (and/or other systems disclosed herein) and the various elements thereof disclosed herein may include those commonly associated with medical devices. For simplicity purposes, the following discussion makes reference to the delivery system 12 and/or the medical implant 14. However, this is not intended to limit the devices and methods described herein, as the discussion may be applied to other elements, members, components, or devices disclosed herein, such as, but not limited to, the anchor member or braid 40, the actuator member 50, the post member 76, the buckle member 58, the pivot pin 20, and/or elements or components thereof.

In some embodiments, the delivery system 12 and/or the medical implant 14, and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system 12 and/or the medical implant 14, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical implant system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical implant system 10 to achieve the same result.

In some embodiments, a degree of Magnetic Resonance Imaging (MRI) compatibility is imparted into the medical implant system 10. For example, the delivery system 12 and/or the medical implant 14, and/or components or portions thereof, may be made of a material that does not substantially distort the image and create substantial artifacts (i.e., gaps in the image). Certain ferromagnetic materials, for example, may not be suitable because they may create artifacts in an MRI image. The delivery system 12 and/or the medical implant 14, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the delivery system 12 that may define a generally smooth outer surface for the medical implant system 10. In other embodiments, however, such a sheath or covering may be absent from a portion of all of the medical implant system 10, such that the delivery system 12 may form an outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, an exterior surface of the medical implant system 10 (including, for example, the exterior surface of the delivery system 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of the delivery system 12, or other portions of the medical implant system 10. Alternatively, the sheath may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A replacement heart valve locking mechanism, comprising:

a buckle member fixedly attached to a tubular anchor member;

a post member axially translatable relative to the buckle member;

a valve leaflet attached to the post member; and an actuator member including a pivot pin proximate a distal end of the actuator member, the actuator member being releasably connected to a proximal end of the post member at the pivot pin;

wherein the post member includes a latch portion configured to engage the buckle member such that movement of the post member distally relative to the buckle member is prevented, wherein the post member is reversibly actuatable between a first orientation, wherein the latch portion extends distally from a body portion of the post member in an everted delivery configuration and a second orientation wherein the latch portion extends proximally from the body portion of the post member.

2. The replacement heart valve locking mechanism of claim 1, wherein the buckle member includes a protrusion configured to release the actuator member from the post member.

3. The replacement heart valve locking mechanism of claim 2, wherein the post member includes two arms spaced apart by a longitudinally-oriented slot, the two arms being configured to releasably engage the actuator member.

4. The replacement heart valve locking mechanism of claim 3, wherein the longitudinally-oriented slot narrows distally.

5. The replacement heart valve locking mechanism of claim 4, wherein the protrusion is configured to splay apart the two arms as the post member is translated proximally.

6. The replacement heart valve locking mechanism of claim 1, wherein the post member includes a cantilevered leg extending proximally from a distal end of the post member.

7. The replacement heart valve locking mechanism of claim 1, wherein the buckle member is substantially rigid.

8. The replacement heart valve locking mechanism of claim 1, wherein the actuator member is pivotable relative to the post member at the pivot pin.

9. The replacement heart valve locking mechanism of claim 1, wherein the latch portion is configured to be deflected by the buckle member as the post member is translated proximally through the buckle member.

10. The replacement heart valve locking mechanism of claim 1, wherein the pivot pin is rigid.

11. A replacement heart valve, comprising:
a tubular anchor member actuatable between an elongated delivery configuration and a deployed configuration;
a buckle member fixedly attached to the anchor member;
a post member axially translatable relative to the buckle member, the post member including a latch portion configured to engage the buckle member when the anchor member is in the deployed configuration;
an actuator member having a first distally displaced delivery position and a second proximally displaced position; and
a valve leaflet attached to the post member;
wherein the post member is everted distal of the anchor member when the anchor member is in the elongated delivery configuration and is disposed within the anchor member when the anchor member is in the deployed configuration.

12. The replacement heart valve of claim 11, wherein the latch portion is configured to engage the buckle member such that movement of the post member distally relative to the buckle member is prevented.

13. The replacement heart valve of claim 11, wherein the post member includes two arms spaced apart by a longitudinally-oriented slot, the two arms being configured to releasably engage the actuator member.

14. The replacement heart valve of claim 13, wherein the longitudinally-oriented slot narrows distally.

15. The replacement heart valve of claim 13, wherein the buckle member includes a protrusion configured to release the actuator member from the post member.

16. The replacement heart valve of claim 15, wherein the protrusion is configured to splay apart the two arms as the post member is translated proximally.

17. The replacement heart valve of claim 11, wherein the post member includes a cantilevered leg extending proximally from a distal end of the post member and the valve leaflet is attached to the cantilevered leg.

18. The replacement heart valve of claim 11, wherein the actuator member includes a flattened body portion configured to axially translate through the buckle member.

19. The replacement heart valve of claim 18, wherein the flattened body portion prevents relative rotation between the actuator member and the buckle member.

20. The replacement heart valve of claim 11, wherein the latch portion is configured to be deflected by the buckle member as the post member is translated proximally through the buckle member.

* * * * *